US009029132B2

(12) United States Patent
Khater et al.

(10) Patent No.: US 9,029,132 B2
(45) Date of Patent: May 12, 2015

(54) SENSOR FOR BIOMOLECULES

(75) Inventors: Marwan H. Khater, Yorktown Heights, NY (US); Tak H. Ning, Yorktown Heights, NY (US); Lidija Sekaric, Yorktown Heights, NY (US); Sufi Zafar, Yorktown Heights, NY (US)

(73) Assignee: International Business Machines Corporation, Armonk, NY (US)

( * ) Notice: Subject to any disclaimer, the term of this patent is extended or adjusted under 35 U.S.C. 154(b) by 468 days.

(21) Appl. No.: 12/537,063

(22) Filed: Aug. 6, 2009

(65) Prior Publication Data

US 2011/0033952 A1 Feb. 10, 2011

(51) Int. Cl.
| | |
|---|---|
| *C12M 1/34* | (2006.01) |
| *G01N 33/551* | (2006.01) |
| *G01N 33/543* | (2006.01) |
| *B82Y 10/00* | (2011.01) |
| *G01N 27/327* | (2006.01) |
| *H01L 29/78* | (2006.01) |

(52) U.S. Cl.
CPC ...... *G01N 33/54373* (2013.01); *G01N 27/3276* (2013.01); *G01N 33/543* (2013.01); *B82Y 10/00* (2013.01); *H01L 29/785* (2013.01); *Y10S 977/953* (2013.01); *Y10S 977/92* (2013.01); *Y10S 977/721* (2013.01)

(58) Field of Classification Search
None
See application file for complete search history.

(56) References Cited

U.S. PATENT DOCUMENTS

| | | | |
|---|---|---|---|
| 3,562,553 A | 2/1971 | Roth | |
| 3,766,371 A * | 10/1973 | Suzuki | 708/702 |
| 4,173,818 A | 11/1979 | Bassous et al. | |
| 4,238,757 A | 12/1980 | Schenck | |
| 4,657,658 A | 4/1987 | Sibald | |
| 4,984,045 A | 1/1991 | Matsunaga | |
| 5,160,597 A | 11/1992 | Colapicchioni et al. | |
| 5,309,085 A | 5/1994 | Sohn | |
| 6,258,606 B1 | 7/2001 | Kovacs | |
| 6,525,354 B2 | 2/2003 | Masleid | |
| 6,682,936 B2 | 1/2004 | Kovacs | |

(Continued)

FOREIGN PATENT DOCUMENTS

| | | |
|---|---|---|
| DE | 10254158 A1 | 6/2004 |
| JP | 2007533987 | 11/2007 |

(Continued)

OTHER PUBLICATIONS

Hinkle et al (2004) Surface Science 566-568: 1185-1189.*

(Continued)

*Primary Examiner* — Chris L Chin
*Assistant Examiner* — Richard Moerschell
(74) *Attorney, Agent, or Firm* — Cantor Colburn LLP; Vazken Alexanian

(57) ABSTRACT

A sensor for biomolecules includes a silicon fin comprising undoped silicon; a source region adjacent to the silicon fin, the source region comprising heavily doped silicon; a drain region adjacent to the silicon fin, the drain region comprising heavily doped silicon of a doping type that is the same doping type as that of the source region; and a layer of a gate dielectric covering an exterior portion of the silicon fin between the source region and the drain region, the gate dielectric comprising a plurality of antibodies, the plurality of antibodies configured to bind with the biomolecules, such that a drain current flowing between the source region and the drain region varies when the biomolecules bind with the antibodies.

14 Claims, 10 Drawing Sheets

(56) References Cited

U.S. PATENT DOCUMENTS

| | | | |
|---|---|---|---|
| 6,911,383 B2* | 6/2005 | Doris et al. | 438/588 |
| 6,956,258 B2 | 10/2005 | Peng | |
| 7,019,305 B2 | 3/2006 | Eversmann et al. | |
| 7,116,113 B1 | 10/2006 | Thompsen et al. | |
| 7,150,997 B2 | 12/2006 | Kovacs | |
| 7,151,301 B2 | 12/2006 | Yoo et al. | |
| 7,291,496 B2 | 11/2007 | Holm-Kennedy | |
| 7,317,216 B2 | 1/2008 | Holm-Kennedy | |
| 7,357,018 B2 | 4/2008 | Curry et al. | |
| 7,394,263 B2 | 7/2008 | Pechstein et al. | |
| 7,507,675 B2 | 3/2009 | Zuilhof et al. | |
| 2002/0158276 A1* | 10/2002 | Masleid | 257/288 |
| 2004/0109075 A1 | 6/2004 | Tsunai | |
| 2004/0256655 A1 | 12/2004 | Kan et al. | |
| 2005/0040483 A1 | 2/2005 | Offenhauser et al. | |
| 2005/0053524 A1 | 3/2005 | Keersmaecker et al. | |
| 2005/0068015 A1 | 3/2005 | Hazucha et al. | |
| 2005/0230271 A1 | 10/2005 | Levon et al. | |
| 2006/0145194 A1 | 7/2006 | Barron et al. | |
| 2006/0181925 A1* | 8/2006 | Specht et al. | 365/185.17 |
| 2006/0246443 A1* | 11/2006 | Bockelmann et al. | 435/6 |
| 2006/0272942 A1 | 12/2006 | Sirringhaus | |
| 2007/0069285 A1* | 3/2007 | Takami | 257/327 |
| 2007/0080440 A1* | 4/2007 | Cheng et al. | 257/684 |
| 2007/0159216 A1 | 7/2007 | Lee et al. | |
| 2007/0252176 A1 | 11/2007 | Shim et al. | |
| 2008/0035494 A1 | 2/2008 | Gomez et al. | |
| 2008/0151088 A1 | 6/2008 | Frey et al. | |
| 2008/0303095 A1* | 12/2008 | Xiong et al. | 257/365 |
| 2008/0315861 A1 | 12/2008 | Chung et al. | |
| 2009/0072313 A1 | 3/2009 | Cai et al. | |
| 2009/0127589 A1 | 5/2009 | Rothberg et al. | |
| 2010/0164102 A1* | 7/2010 | Rachmady et al. | 257/741 |
| 2010/0248284 A1* | 9/2010 | Chen et al. | 435/29 |
| 2011/0033952 A1 | 2/2011 | Khater et al. | |

FOREIGN PATENT DOCUMENTS

| | | | | |
|---|---|---|---|---|
| WO | 2008068719 A1 | | 6/2008 | |
| WO | WO 2008/068719 | * | 6/2008 | H01L 29/06 |

OTHER PUBLICATIONS

Papadopoulos (2000) Biophys J. 79(4): 2084-2094.*

Lee (2009) Sensors 2009, 9, 7111-7131.*

Han, Label-free detection of biomlecules by a field-effect transistor microarray biosensor with bio-functionalized gate surfaces, Dec. 2006 [retrieved on Mar. 17, 2011]. Retrieved from the internet:,URL:http://juwel.fz-juelich.de:8080/dspace/bitstream/2128/2597/1/Juel_4227_Han.pdf.

Notification of Transmittal of the International Search Report and the Written Opinion of the International Searching Authority, or the Declaration; PCT/US11/20007;Apr. 6, 2011.

U.S. Appl. No. 12/651,504. Non Final Office Action Mailed Mar. 4, 2011.

Lee, et al., Ion-Sensitive Field-Effect Transistor for Biological Sensing, Sensors 2003, 9, 7111-7131; doi:10.3390/s90907111 [online], Sep. 7, 2009 [retrieved on Mar. 17, 2011]. Retrieved from the Internet:,URL:http://www.mdpi.com/1424-8220/9/7111/pdf.

Maher, Electrical Engineering 234 Electrical Engineering Circuit Laboratory, Manual [online], Jun. 1992 [retrieved on Mar. 17, 2011]. Retrieved from the Internet:,URL:http://www.coe.montana.edu/ee/rmaher/teaching/EEngr_234_Labs_maher.pdf>p. 8-1 to 8-20.

O. Hayden et al., Electrical detection of single viruses, PNAS, Sep. 28, 2004, pp. 14017-14022, vol. 101, No. 39, PNAS.

Y. Choi et al., A dielectric-modulated field-effect transistor for biosensing, Nature Nanotechnology, Jul. 2007, pp. 430-434, vol. 2, Nature Publishing Group.

International Search Report and Written Opinion ; International Application No. PCT/EP2011/052981; International Filing Date: Mar. 1, 2011; Date of Mailing: Jun. 30, 2011; 10 pages.

F. Patolsky et al., Electrical detection of single viruses, PNAS, Sep. 28, 2004, pp. 14017-14022, vol. 101, No. 39, PNAS.

H. Im et al., A dielectric-modulated field-effect transistor for biosensing, Nature Nanotechnology, Jul. 2007, pp. 430-434, vol. 2, Nature Publishing Group.

Huang, et al. "Development of Active Matrix Biosensor Array for Cell Screening", Proceedings of IEEE Sensors 2004, Oct. 24-27, 2004, vol. 1, pp. 72-75.

K. Nakazato, et al. "CMOS Cascode Source-Drain Follower for Monolithically Integrated Biosensor Array". IEICE Trans. Electron., vol. E91-C, No. 9 Sep. 2008. pp. 1505-1515.

Leobandung, E., et al.; "Wire-Channel and Wrap-Around-Gate Metal-Oxide-Semiconductor Field-Effect Transistors With a Significant Reduction of Short Channel Effects"; J. Vac. Sci. Technol. B.; vol. 15, No. 6; p. 2791-2794; Nov./Dec. 1997.

Thewes, et al. "CMOS-based Biosensor Arrays". IEEE Computer Society, Proceedings of the Design, Automation and Test in Europe Conference and Exhibition Mar. 7-11, 2005, vol. 2, pp. 1222-1223.

Simpson, Robert E.; "Introductory Electronics for Scientists and Engineers"; Second Edition; Chapter 6, Allyn and Bacon; p. 258-284; 1987.

Stern, et al; "Label-Free Immunodetection With CMOS-Compatible Seminconducting Nanowires"; Nature; vol. 445; p. 519-522; Feb. 2007.

Wu, et al.; "Single-Crystal Metallic Nanowires and Metal/Semiconductor Nanowire Heterostructures"; Letters to Nature; vol. 430; p. 61-65; Jul. 2004.

Examination Report under Section 18(e) for Application GB1207849.9; Date of Report: Aug. 21, 2013; 7 pgs.

* cited by examiner

900

```
COAT GATE DIELECTRIC WITH ANTIBODIES THAT SELECTIVELY BIND BIOMOLECULES
901
```
```
BRING GATE DIELECTRIC SURFACE INTO CONTACT WITH ELECTRODE DIPPED IN
ELECTROLYTE
902
```
```
APPLY VOLTAGE AT DRAIN, AND SET SOURCE VOLTAGE TO 0V
903
```
```
APPLY GATE VOLTAGE AT ELECTRODE, AND OPTIONALLY APPLY BACK GATE
VOLTAGE FOR THRESHOLD TUNING
904
```
```
MEASURE DRAIN CURRENT
905
```
```
ADD BIOMOLECULES TO ELECTROLYTE
906
```
```
MEASURE CHANGE IN DRAIN CURRENT DUE TO BIOMOLECULES
907
```

```
┌─────────────────────────────────────────────────────────────────────────┐
│   BRING GATE DIELECTRIC SURFACE INTO CONTACT WITH ELECTRODE DIPPED IN   │
│                              ELECTROLYTE                                │
│                                 1001                                    │
└─────────────────────────────────────────────────────────────────────────┘
```
```
┌─────────────────────────────────────────────────────────────────────────┐
│   BRING GATE DIELECTRIC SURFACE INTO CONTACT WITH MEMBRANE EMBEDDED     │
│                           WITH BIOMOLECULES                             │
│                                 1002                                    │
└─────────────────────────────────────────────────────────────────────────┘
```
```
┌─────────────────────────────────────────────────────────────────────────┐
│             APPLY VOLTAGE AT DRAIN, AND SET SOURCE VOLTAGE TO 0V        │
│                                 1003                                    │
└─────────────────────────────────────────────────────────────────────────┘
```
```
┌─────────────────────────────────────────────────────────────────────────┐
│     APPLY GATE VOLTAGE AT ELECTRODE, AND OPTIONALLY APPLY BACK GATE     │
│                      VOLTAGE FOR THRESHOLD TUNING                       │
│                                 1004                                    │
└─────────────────────────────────────────────────────────────────────────┘
```
```
┌─────────────────────────────────────────────────────────────────────────┐
│                          MEASURE DRAIN CURRENT                          │
│                                 1005                                    │
└─────────────────────────────────────────────────────────────────────────┘
```
```
┌─────────────────────────────────────────────────────────────────────────┐
│  ADD MOLECULES THAT CAUSE PORES IN ION CHANNELS OF MEMBRANE TO OPEN,    │
│              CAUSING A LOCALIZED CHANGE IN ION DENSITY                  │
│                                 1006                                    │
└─────────────────────────────────────────────────────────────────────────┘
```
```
┌─────────────────────────────────────────────────────────────────────────┐
│        MEASURE CHANGE IN DRAIN CURRENT DUE TO CHANGE IN ION DENSITY     │
│                                 1007                                    │
└─────────────────────────────────────────────────────────────────────────┘
```

FIG. 10

SENSOR FOR BIOMOLECULES

FIELD OF INVENTION

This disclosure relates generally to the field of sensors for biomolecule detection.

DESCRIPTION OF RELATED ART

Biomolecules, which may include proteins or viruses, play an important role in many illnesses; the study of biomolecules is essential for improved, cost effective disease diagnosis and treatment. Some methods that may be used to detect biomolecules include fluorescence or radioactive labeling, and patch clamp. However, these methods may be labor intensive, costly, or have limited sensitivity. Such detection methods may also be difficult to integrate into systems that include additional functionality such as sample delivery, data acquisition, or data transmission. For example, the patch clamp method is used for sensing proteins such as ion channels that are embedded in the membrane of a cell. This method includes a pipette that punctures the cell membrane embedded with proteins. Due to the presence of the pipette, the patch clamp method has limited scope for miniaturization or integration onto a multifunctional platform.

A field effect transistor (FET) based sensor, such as large area planar FET or a back-gated silicon nanowire FET, may be used to detect biomolecules by measuring the drain current in the sub-threshold regime where the drain current has an exponential dependence on the gate voltage of the FET. A large area planar FET may have limited sensitivity, and may therefore detect only high concentrations of biomolecules. A back-gated silicon nanowire FET exhibits improved sensitivity in comparison to large area planar FET based sensors. In a back-gated silicon nanowire FET, silicon nanowire forms the sensing surface, buried oxide act as the gate dielectric and silicon substrate act as the gate. The sensitivity of a back-gated nanowire FET may be degraded due to two factors: a large sub-threshold slope due to the thick buried oxide that acts as the gate dielectric, and formation of the inversion layer at the silicon/oxide interface such that is located away from the sensing surface of the silicon channel. Since these factors are inherent structural features of a back-gated silicon nanowire FET, its sensitivity can only enhanced by reducing the silicon nanowire thickness. However, reduction in silicon nanowire thickness causes the sensing area to decrease, resulting in slower response times, and also making the wires relatively fragile. In summary, back-gated silicon nanowire FET sensors have an inherent structural design disadvantage for biomolecule sensing applications.

SUMMARY

In one aspect, a sensor for biomolecules includes a silicon fin comprising undoped silicon; a source region adjacent to the silicon fin, the source region comprising heavily doped silicon; a drain region adjacent to the silicon fin, the drain region comprising heavily doped silicon of a doping type that is the same doping type as that of the source region; and a layer of a gate dielectric covering an exterior portion of the silicon fin between the source region and the drain region, the gate dielectric comprising a plurality of antibodies, the plurality of antibodies configured to bind with the biomolecules, such that a drain current flowing between the source region and the drain region varies when the biomolecules bind with the antibodies.

In one aspect, a method for sensing biomolecules in an electrolyte includes exposing a gate dielectric surface of a silicon fin, the gate dielectric surface comprising antibodies configured to bind with the biomolecules, to an electrolyte comprising the biomolecules; applying a gate voltage to an electrode immersed in the electrolyte; and measuring a change in a drain current flowing in the silicon fin to determine whether biomolecules are present in the electrolyte.

In one aspect, a method for sensing biomolecules in a membrane includes bringing a gate dielectric surface of a silicon fin into contact with a membrane comprising the biomolecules, the membrane being immersed in an electrolyte; applying a gate voltage to an electrode immersed in the electrolyte; adding molecules to the electrolyte, the molecules configured to cause pores in the membrane to open; and measuring a change in a drain current flowing in the silicon fin to determine whether biomolecules are present in the membrane.

Additional features are realized through the techniques of the present exemplary embodiment. Other embodiments are described in detail herein and are considered a part of what is claimed. For a better understanding of the features of the exemplary embodiment, refer to the description and to the drawings.

BRIEF DESCRIPTION OF THE SEVERAL VIEWS OF THE DRAWINGS

Referring now to the drawings wherein like elements are numbered alike in the several FIGURES:

FIG. 9 illustrates an embodiment of a method for detection of biomolecules in an electrolyte using a sensor.

FIG. 10 illustrates an embodiment of a method for detection of biomolecules in a membrane using a sensor.

DETAILED DESCRIPTION

Embodiments of systems and methods for a sensor for biomolecules are provided, with exemplary embodiments being discussed below in detail. A structure for FET based sensor is proposed which overcomes the drawbacks of back-gated silicon nanowire FET sensor as described in above. Consequently, the proposed sensor structure may have significantly improved sensitivity, larger sensing area and higher yield in comparison to a back-gated silicon nanowire FET.

A sensor for biomolecules, which may include, but are not limited to, proteins or viruses, may comprise a FET-type structure comprising one or more silicon fins. The silicon fin structure may have a low sub-threshold slope (SS), an inversion layer formed close to the sensing surface, and volume inversion effects, which may act to increase the sensitivity of the sensor. Response time of the sensor may also be reduced. The sensor structure may be fabricated using standard silicon process technology, allowing the sensor to be cost effectively mass produced and easily integrated into a multi-function silicon chip that performs such functions as sample delivery, data acquisition, or data transmission.

A FET-based sensor may detect biomolecules by measuring the drain current ($I_d$) of the FET structure in the sub-threshold regime, where $I_d$ has exponential dependence on a gate voltage. The majority of biomolecules are charged, therefore, when a charged biomolecule is in the vicinity of a silicon channel of the FET structure, the biomolecule may cause the drain current to change by $\Delta I_d$, where $$\Delta I_d = \mu * C_{ox}/SS,$$

where $C_{ox}$ is the gate oxide capacitance, $\mu$ is the mobility of electrons or holes in the silicon channel, and SS is the sub-threshold slope. Since $\Delta I_d$ is a measure of sensor sensitivity, the sensitivity may be maximized by utilization of a FET structure that has a relatively small sub-threshold slope and relatively large $C_{ox}$ and $\mu$ values.

The silicon fin width and height may be adjusted so as to obtain a SS of about 62 mV/decade. Response time of the sensor may also be reduced by increasing the surface area of a silicon fin. A reduction in response time without degradation of sensitivity may be obtained by a channel length ($L_g$) of a silicon fin that is greater than about 0.5 micron (µm), a silicon fin width ($W_{si}$) that is less than about 30 nanometers (nm), and a silicon fin height ($H_{si}$) that is greater than or equal to twice $W_{si}$. A $W_{si}$ of less than about 25 nm may result in a volume inversion effect, which may cause mobility (µ) to increase. The gate dielectric may comprise a layer of SiO2 or SiON, or a stack consisting of SiON and metal oxide insulator such as HfO2, with an equivalent oxide thickness of about 5 nm. An electrolyte may act as the top FET gate. The gate dielectric may be covered with antibodies that selectively bind with the biomolecules to be detected in some embodiments.

Figure 1:
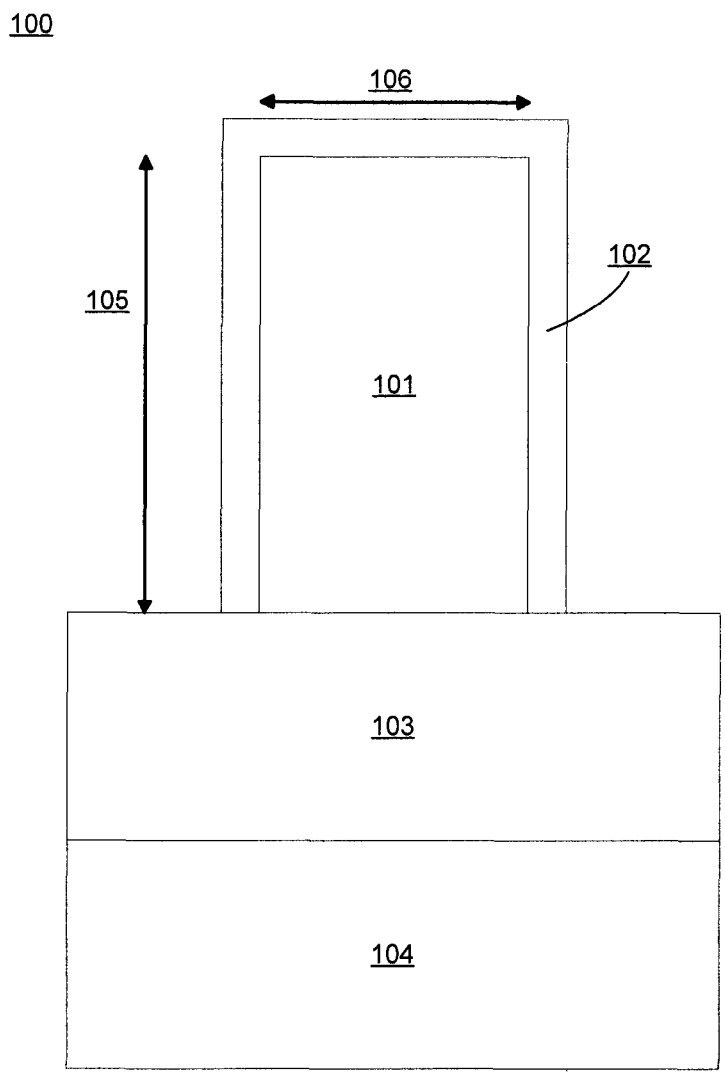
FIG. 1 illustrates a cross section of an embodiment of a fin FET based sensor for biomolecules.

FIG. 1 illustrates a cross-section of an embodiment of a fin FET based sensor 100 for biomolecules. Silicon fin 101 comprises undoped silicon. Silicon fin 101 is coated with gate dielectric 102. Gate dielectric layer 102 forms the biomolecule detection surface, and may comprise oxide/HfO2 stack or SiON in some embodiments. The gate dielectric layer 102 further comprises antibodies that selectively bind with the biomolecules to be detected in some embodiments. Buried oxide layer 103 and silicon back gate 104 form a base of the sensor 100. Line 105 illustrates the silicon fin height ($H_{si}$), and line 106 illustrates the silicon fin width ($W_{si}$).

Figure 2:
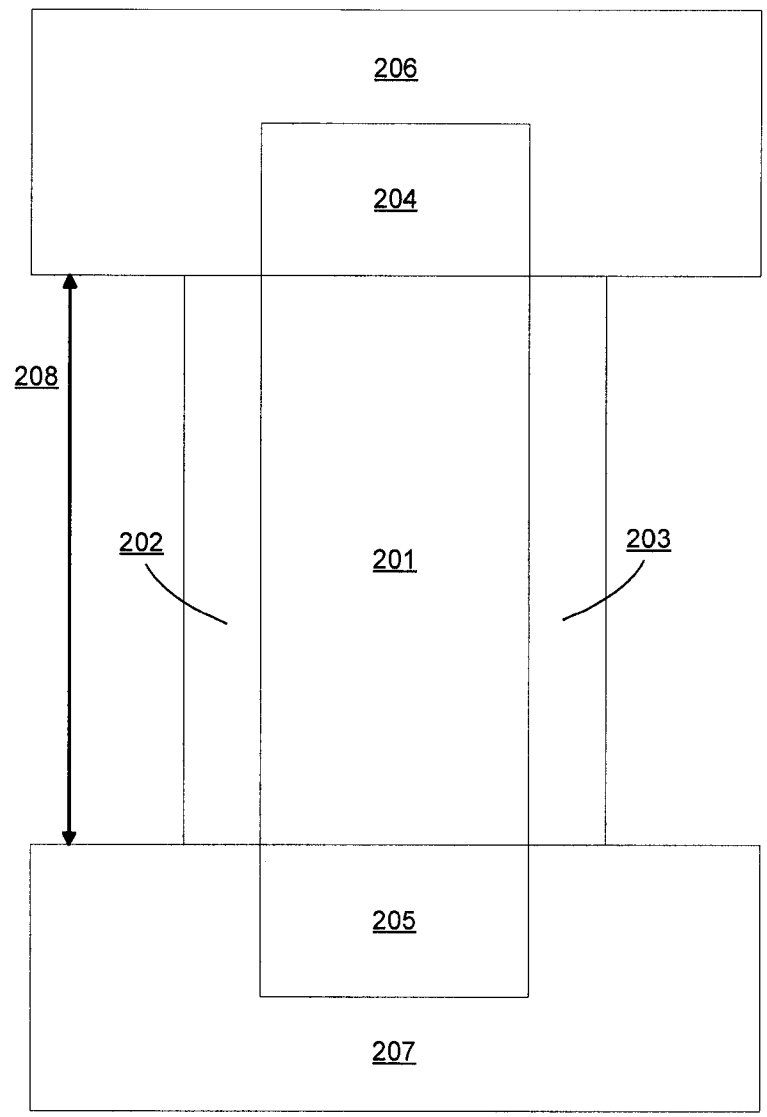
FIG. 2 illustrates a top view of an embodiment of a fin FET based sensor for biomolecules.

FIG. 2 illustrates a top view of an embodiment of a fin FET based sensor 200 for biomolecules. Silicon fin 201 comprises a channel of undoped silicon, and has a channel length ($L_g$) illustrated by line 208. Gate dielectric layers 202 and 203 form the biomolecule detection surface, and comprise oxide/HfO2 stack or SiON in some embodiments. The gate dielectric layers 202 and 203 further comprise antibodies that selectively bind with the biomolecules to be detected in some embodiments. Drain 204 comprises heavily doped n+ or p+ silicon, and source 205 comprises heavily doped silicon of the same doping type as the drain. Regions 206 and 207 comprise thick oxide layers that act to isolate the drain 204 and source 205 from an electrolyte containing biomolecules that covers the gate dielectric layers 202 and 203 in operation.

Figure 3:
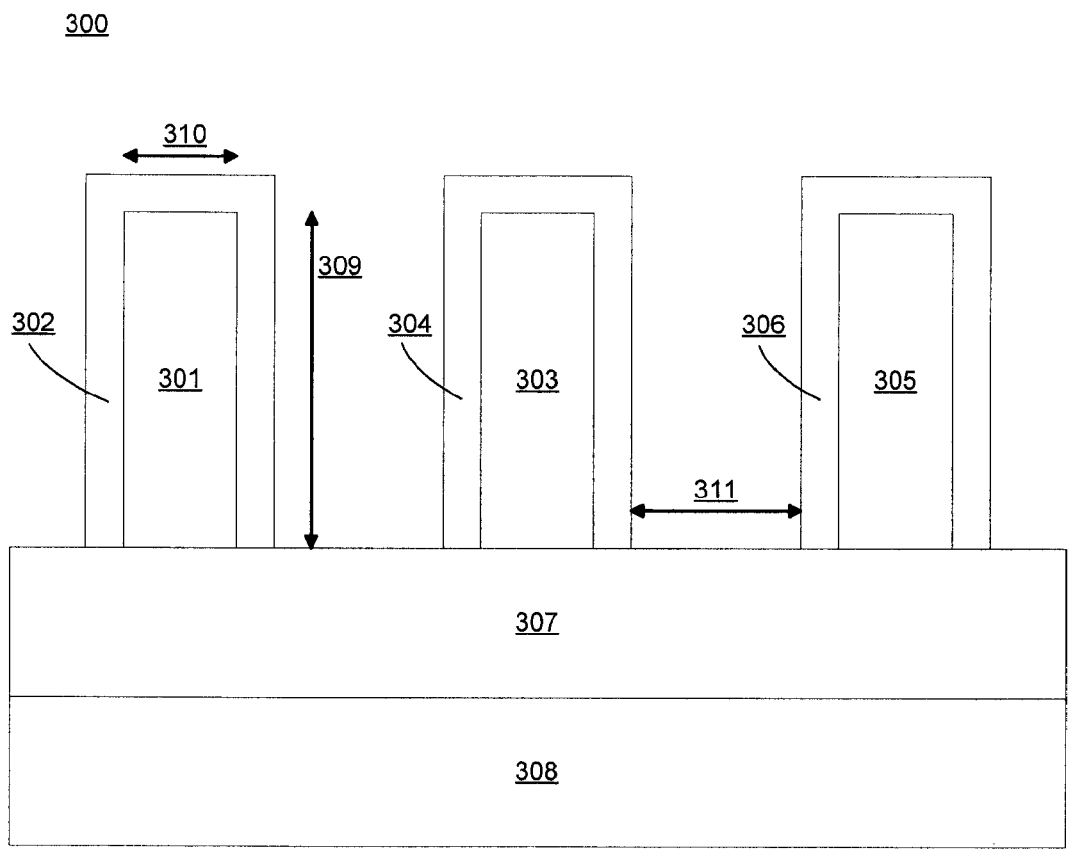
FIG. 3 illustrates a cross section of an embodiment of a sensor for biomolecules comprising multiple fin FETs.

Some embodiments may comprise multiple fin FETs, which reduce the response time of the sensor by increasing the detection surface area. FIG. 3 illustrates an embodiment of a cross-section of a sensor 300 for biomolecules comprising multiple fin FETs. Silicon fins 301, 303, and 305 comprise undoped silicon. Silicon fins 301, 303, and 305 are coated with gate dielectric layers 302, 304, and 306. Gate dielectric layers 302, 304, and 306 form the biomolecule detection surface, and may comprise oxide/HfO2 stack or SiON in some embodiments. The gate dielectric layers 302, 304, and 306 further comprise antibodies that selectively bind with the biomolecules to be detected in some embodiments. Buried oxide layer 307 and silicon back gate 308 form the base of the sensor 300. Line 309 illustrates the silicon fin height ($H_{si}$), line 310 illustrates the silicon fin width ($W_{si}$), and line 311 illustrates the spacing between fins. Three fin FETs are shown in the embodiment of FIG. 3 for illustrative purposes only; any appropriate number of fin FETs may comprise a sensor for biomolecules.

Figure 4:
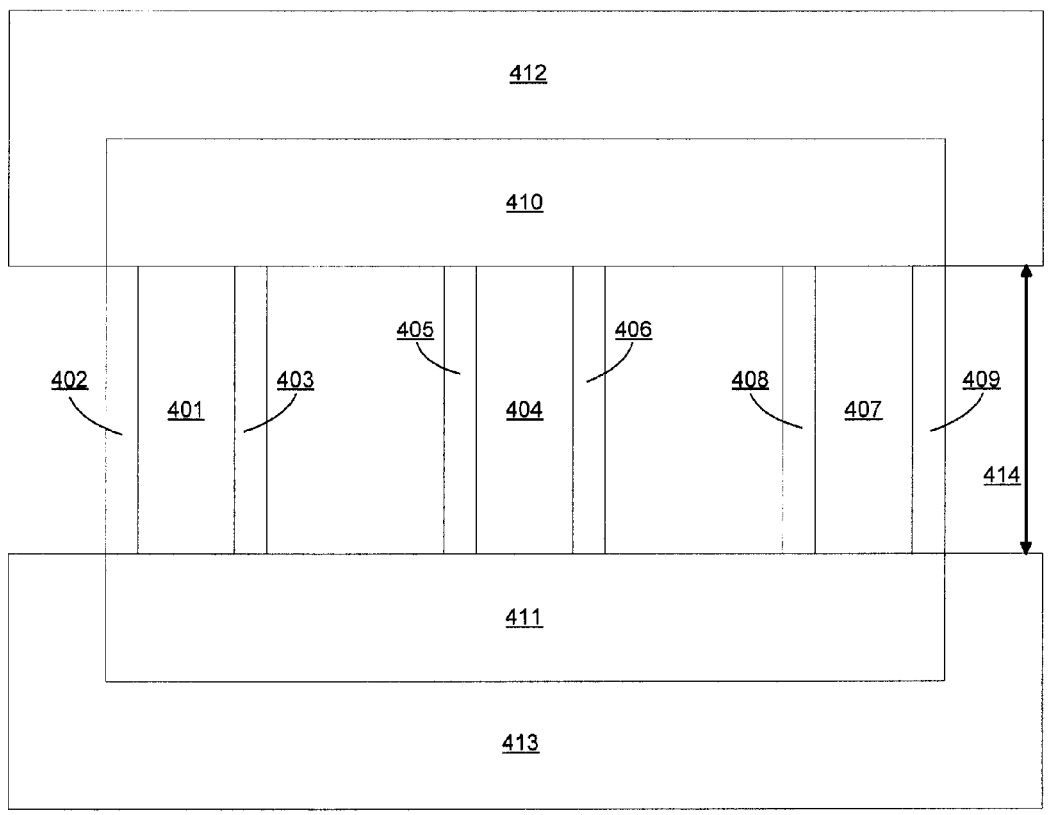
FIG. 4 illustrates a top view of an embodiment of a sensor for biomolecules comprising multiple fin FETs.

FIG. 4 illustrates a top view of an embodiment of a sensor 400 for biomolecules comprising multiple fin FETs. Silicon fins 401, 404, and 407 comprise channels of undoped silicon having a channel length ($L_g$) illustrated by line 414. Gate dielectric layers 402, 403, 405, 406, 408, and 409 form the biomolecule detection surface, and comprise oxide/HfO2 stack or SiON in some embodiments. The gate dielectric layers 402, 403, 405, 406, 408, and 409 further comprise antibodies that selectively bind with the biomolecules to be detected in some embodiments. Drain 410 comprises heavily doped n+ or p+ silicon, and source 411 comprises heavily doped silicon of the same doping type as the drain. Regions 412 and 413 comprise thick oxide layers that act to isolate the drain 410 and source 411 from an electrolyte containing biomolecules that covers the gate dielectric layers 402, 403, 405, 406, 408, and 409 in operation. Three fin FETs with common source and drain regions 410 and 411 are shown in the embodiment of FIG. 4 for illustrative purposes only; any appropriate number of fin FETs may comprise a sensor for biomolecules.

Figure 5:
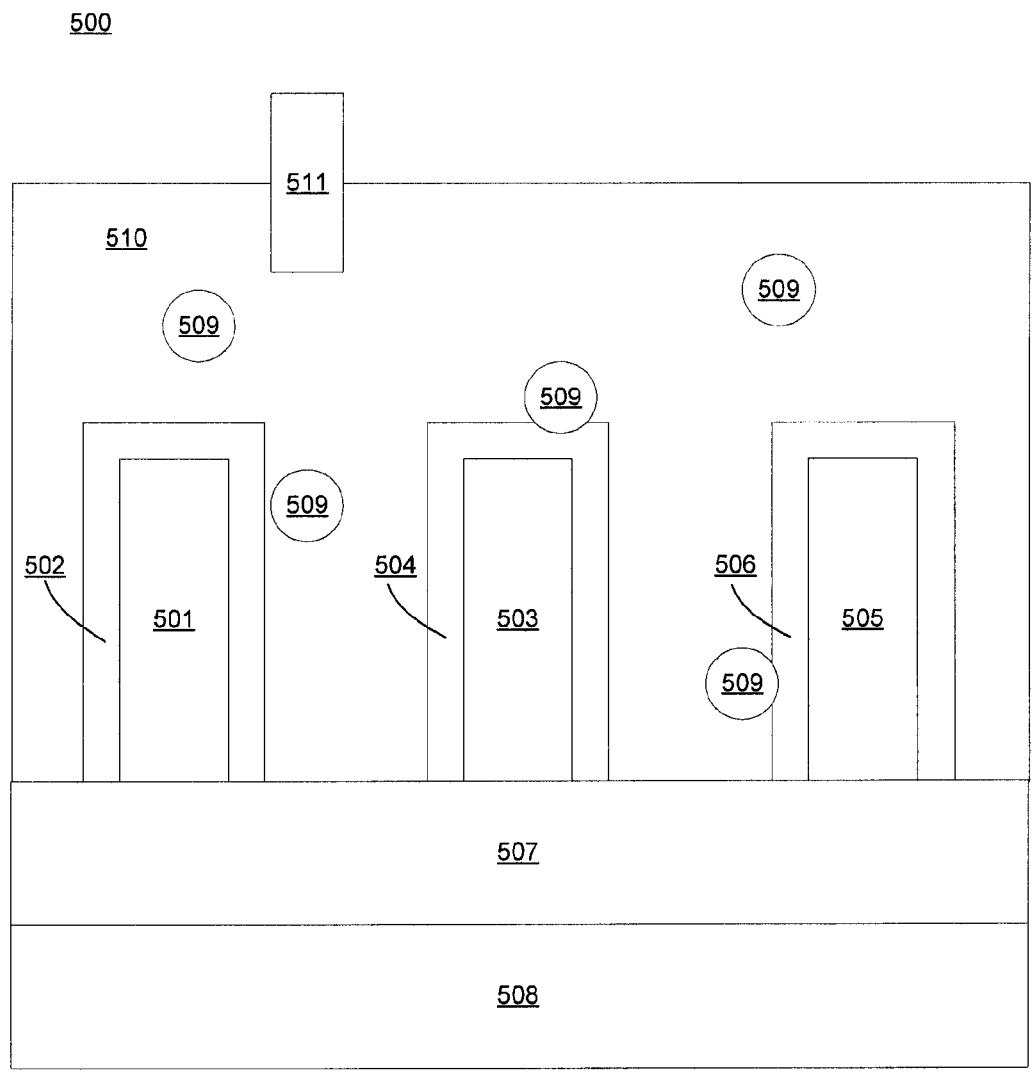
FIG. 5 illustrates a cross-section of an embodiment of a sensor for biomolecules comprising multiple fin FETS.

FIG. 5 illustrates a cross-section of an embodiment of a sensor 500 for biomolecules comprising multiple fin FETs that is immersed in an electrolyte solution 510 comprising biomolecules 509. Fins 501, 503, and 505 are coated in gate dielectric 502, 504, and 506. Buried oxide layer 507 and silicon back gate 508 form a base of sensor 500. Electrolyte solution 510 acts as the FET top gate. Biomolecules 509 bind with antibodies located on gate dielectric 502, 504, and 506, causing a change ($\Delta I_d$) in the drain current ($I_d$) of the sensor 500, allowing the biomolecules 509 to be detected. The gate voltage is supplied by an electrode 511, which comprises a silver wire coated with silver chloride in some embodiments. The back gate 508 may have the same polarity bias as the electrolyte 510, or the back gate 508 may be grounded. Top gate electrolyte 510 is in the sub-threshold regime. For the case of n-type source and drain regions, a positive polarity voltage is applied at the drain, the source voltage is held at 0V and a voltage between approximately 100 mV and 3V is applied at electrode 511, causing a drain current to flow between the source and drain of the sensor (source and drain are discussed above, see, for example, elements 204 and 250 of FIG. 2, and elements 410 and 411 of FIG. 4). When biomolecules 509 attaches to gate dielectric layers 502, 504, and 506, the drain current changes according to the charge of the biomolecules, allowing detection of the biomolecules. Three fin FETs are shown in the embodiment of FIG. 5 for illustrative purposes only; any appropriate number of fin FETs may comprise a sensor for biomolecules.

A sensor structure may comprise a single fin FET or multiple fin FETs with common source and drain depending on whether sensitivity or response time is a more important for a particular biomolecule detection application. If higher sensitivity is desired, a single fin FET structure may be used, whereas multiple fin FETs reduce the response time. The spacing between the fin FETs in a multiple fin FET embodiment may be adjusted so as to provide size selectivity for detecting biomolecules. For example, for a sensor configured to detect a virus with a diameter of approximately 100 nm, the spacing between fin FETs may be made slightly (approximately 5%-20%) larger than the diameter of the virus to be detected. Any appropriate number of fin FETs may comprise an embodiment of a sensor for biomolecules.

Figure 6:
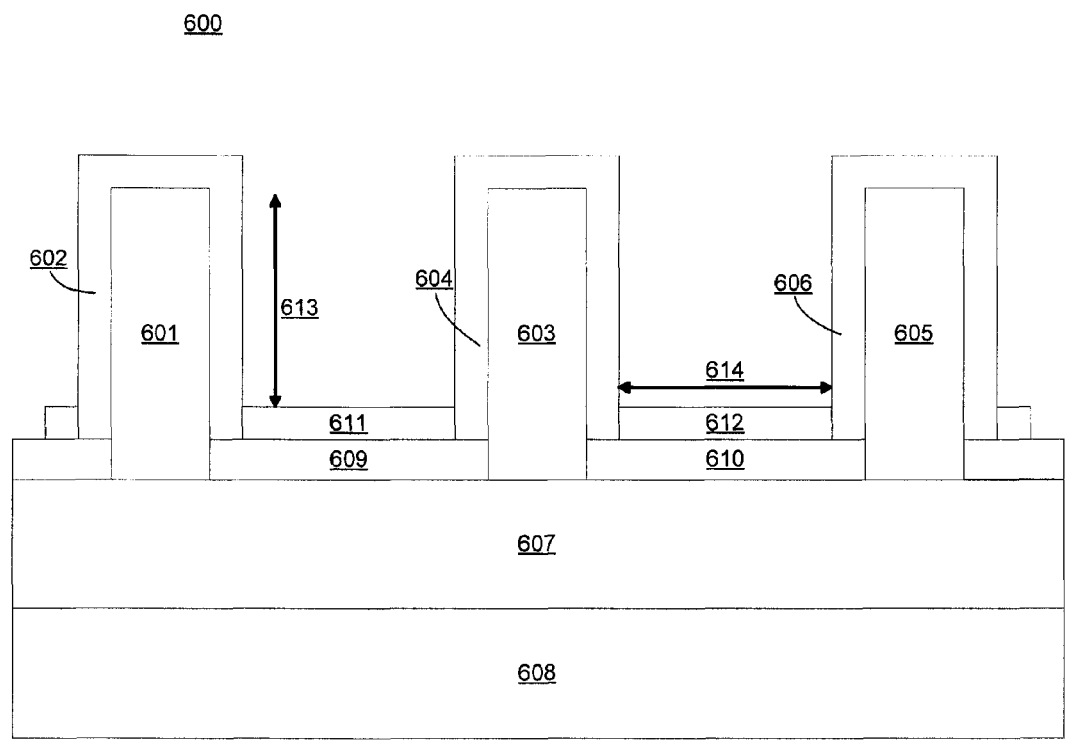
FIG. 6 illustrates a cross-section of an embodiment of a sensor for biomolecules comprising fin and planar FETs.

FIG. 6 illustrates a cross-sectional view of an embodiment of a sensor 600 comprising fin and planar FETs. Planar FETs 609 and 610 comprise extremely thin planar silicon layers; planar FETs 609 and 610 are located between adjacent fin FETs 601 and 603, and 603 and 605, respectively. Line 613 illustrates the silicon fin FET height ($H_{si}$). Planar silicon FETs 609 and 610 comprise undoped silicon of a thickness that is less than $H_{si}$, and may be less than 10 nm in some embodiments. The width of planar silicon FETs 609 and 610 is illustrated by line 614, which is of approximately the same width as the spacing between silicon fins 603 and 605. Planar silicon FETs 609 and 610 and fin FETs 601, 603, and 605 are coated with gate dielectric 602, 604, 606, 611, and 612. Gate dielectric layers form the biomolecule detection surface, and comprise oxide/HfO2 stack or SiON in some embodiments. The gate dielectric layers comprise antibodies that selectively bind with the biomolecules to be detected in some embodiments. Buried oxide layer 607 and silicon back gate 608 form a base of sensor 600. Three fin FETs and two planar FETs are shown in the embodiment of FIG. 6 for illustrative purposes only; any appropriate number of fin and planar FETs may comprise a sensor for biomolecules.

Figure 7A:
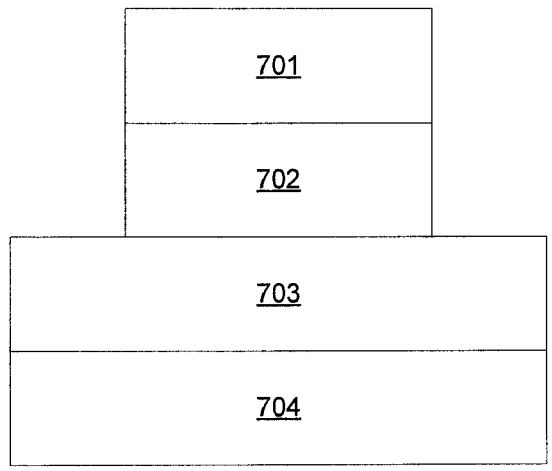
FIG. 7A illustrates a cross-section of the sensor for biomolecules comprising a planar FET that is located between two adjacent fin FETs.
Figure 7B:
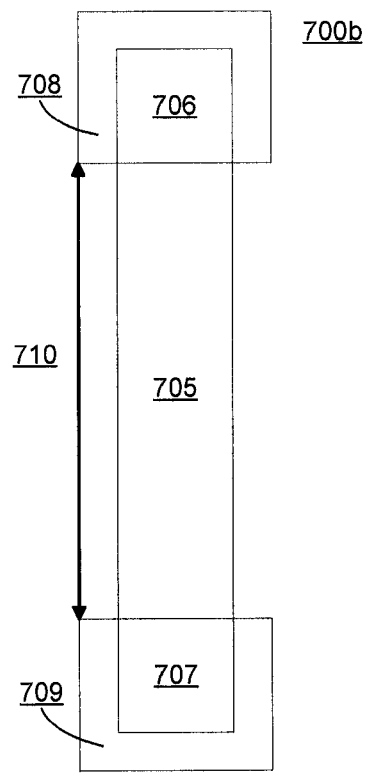
FIG. 7B illustrates a top view of the sensor for biomolecules comprising a planar FET that is located between two adjacent fin FETs.

FIG. 7A illustrates a cross-sectional view 700a of a sensor comprising a planar FET, and FIG. 7B illustrates a top view 700b of a sensor comprising a planar FET. Referring to FIG. 7A, Gate dielectric layer 701 covers planar silicon 702, which is disposed on buried oxide layer 703 and back gate 704. Referring to FIG. 7B, source region 707 is located at one end of planar silicon 705, and drain region 706 is located at the opposite end of planar silicon 705. Drain 706 comprises heavily doped n+ or p+ silicon, and source 707 comprises heavily doped silicon of the same doping type as the drain. Source region 707 and drain region 706 are insulated by thick oxide regions 708 and 709. Planar silicon 705 is covered with a gate dielectric, and has a channel length $L_g$ illustrated by line 710, which is approximately equal to the channel length of a silicon fin, as illustrated by element 208 of FIG. 2.

Figure 8:
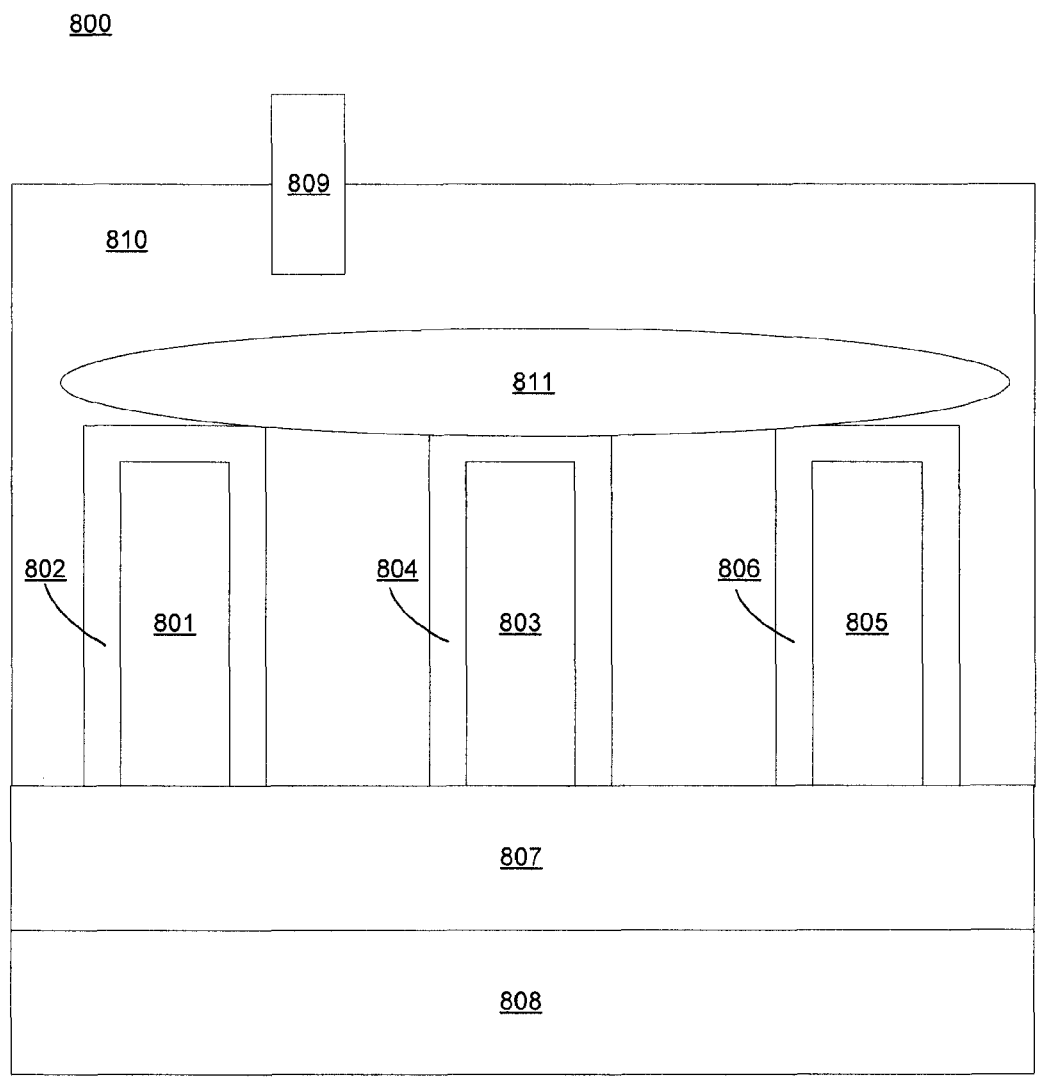
FIG. 8 illustrates a cross-section of an embodiment of a sensor for biomolecules embedded in a membrane.

FIG. 8 illustrates a side view of an embodiment of a sensor 800 configured to detect biomolecules in a membrane 811. Membrane 811 may contain embedded biomolecules such as ion channel or ion pump proteins. Electrolyte 810 acts as the top FET gate. Fins 801, 803, and 805 are coated in gate dielectric 802, 804, and 806. Buried oxide layer 807 and silicon back gate 808 form a base of sensor 800. The gate voltage is supplied at electrode 809, which may comprise silver wire coated with silver chloride in some embodiments. The back gate 808 may have the same polarity bias as the membrane, or be grounded. Three fins are shown in the embodiment of FIG. 8 for illustrative purposes only; any appropriate number of fins may comprise a sensor for biomolecules.

FIG. 9 illustrates an embodiment of a method 900 for detection of biomolecules using a sensor. In block 901, a gate dielectric surface of a silicon fin is coated with antibodies that selectively bind a protein or virus to be detected. In block 902, the gate dielectric surface is brought into contact with an electrode dipped in an electrolyte. The electrolyte acts as a FET gate. In block 903, a voltage is applied at the sensor drain, and the sensor source voltage is set to 0V. In block 904, a gate voltage ($V_g$) is applied at the electrode. A voltage ($V_b$) may also be applied to the back gate for threshold voltage tuning in some embodiments. In block 905, the drain current $I_d$ in the absence of biomolecules is measured. In block 906, the biomolecules are added to the electrolyte. In block 907, the biomolecules bind to the antibodies on the gate dielectric surface, thereby cause the drain current $I_d$ in the sub-threshold regime of the sensor to change by $\Delta I_d$, and the bio-molecules to be detected according to $\Delta I_d$.

FIG. 10 illustrates an embodiment of a method 1000 for detecting biomolecules embedded in the membrane of a cell. In block 1001, the gate dielectric surface is brought into contact with an electrode dipped in an electrolyte. In block 1002, a membrane embedded with biomolecules such as ion channel proteins is brought into contact with the gate dielectric surface. In block 1003, a voltage is applied at the drain, and the source voltage is set to 0V. In block 1004, a gate voltage ($V_g$) is applied at the electrode. A voltage ($V_b$) may also be applied to the back gate for threshold voltage tuning in some embodiments. In block 1005, the drain current $I_d$ is measured. In block 1006, liagand molecules are added to the electrolyte; the liagand molecules cause the pores in the ion channels of the membrane to open, causing ions to flow in or out of the cell, causing a localized change in ion density. In block 1007, the drain current $I_d$ in the sub-threshold regime of the sensor is measured to determine the $\Delta I_d$ caused by the change in ion density caused by the opening of ion channel proteins. While the embodiment of FIG. 10 has been described with reference to liagand gated ion channel proteins, a similar procedure may be used for voltage gated ion channel proteins or ion pump proteins.

The technical effects and benefits of exemplary embodiments include providing a biomolecule sensor with relatively low response time and high sensitivity. The sensor may be relatively cheap to manufacture, and easy to integrate into a multi-functional silicon chip.

The terminology used herein is for the purpose of describing particular embodiments only and is not intended to be limiting of the invention. As used herein, the singular forms "a", "an", and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated. Specifically, while an n-type FET-sensor embodiment was chosen to explain the principles of the invention, the principles of the invention also apply to embodiments comprising p-type FET-sensors.

The invention claimed is:

1. A sensor for biomolecules, comprising:
a plurality of silicon fins comprising undoped silicon;
a source region adjacent to each of the plurality of silicon fins, the source region comprising heavily doped silicon;
a drain region adjacent to each of the plurality of silicon fins, the drain region comprising heavily doped silicon of a doping type that is the same doping type as that of the source region;
a layer of a gate dielectric comprising a dielectric material covering an exterior portion of each of the plurality of silicon fins between the source region and the drain region, the gate dielectric further comprising a plurality of antibodies, the plurality of antibodies configured to bind with the biomolecules, such that a drain current flowing between the source region and the drain region in the silicon fin varies when the biomolecules bind with the antibodies; and
a planar field effect transistor (FET) located between each pair of adjacent silicon fins having a width approximately equal to a distance separating the adjacent silicon fins, the planar FET comprising:
a thin planer silicon layer coated with the gate dielectric material,
wherein the planar FET has a thickness of less than about 10 nm, a width of approximately five to twenty percent larger than a diameter of the biomolecules to be sensed, and a channel length that is about equal to a channel length of a the silicon fin,
wherein the silicon fin has a width of less than about 25 nanometers (nm) and a height greater than or equal to about twice the width, and
wherein the gate dielectric material substantially covers an upper surface of the sensor.

2. The sensor for biomolecules of claim 1, wherein the silicon fin has a channel length of greater than about 0.5 microns (μm).

3. The sensor for biomolecules of claim 1, wherein the dielectric material that comprises the gate dielectric comprises SiON/HfO$_2$, and has a thickness of less than about 10 nm.

4. The sensor for biomolecules of claim 1, wherein the sensor comprises a fin field effect transistor (finFET), and the silicon fin comprises a channel of the finFET; and
further comprising an electrolyte containing the biomolecules, the electrolyte comprising a gate of the finFET, wherein the electrolyte is separated from the silicon fin by the dielectric material of the gate dielectric.

5. The sensor for biomolecules of claim 4, further comprising an electrode immersed in the electrolyte.

6. The sensor for biomolecules of claim 4, wherein a gate voltage in a sub-threshold regime is applied at the electrode.

7. The sensor for biomolecules of claim 4, further comprising a membrane containing biomolecules immersed in the electrolyte.

8. The sensor for biomolecules of claim 4, further comprising an oxide layer configured to insulate the drain region from the electrolyte, and an oxide layer configured to insulate the source region from the electrolyte.

9. The sensor for biomolecules of claim 1, further comprising an electrolyte containing the biomolecules, the electrolyte comprising a gate of the finFET comprising the sensor.

10. The sensor for biomolecules of claim 3, wherein the silicon fin, source region, and drain region are located on a buried oxide layer, and further comprising a silicon back gate located underneath the buried oxide layer on a side of the buried oxide layer opposite to the silicon fin, source region, and drain region.

11. The sensor for biomolecules of claim 10, wherein the silicon back gate has a bias configured to adjust a threshold voltage of the sensor.

12. The sensor for biomolecules of claim 10, wherein the silicon back gate is grounded.

13. The sensor for biomolecules of claim 1, wherein the antibodies are located on an outer surface of the dielectric material that comprises the gate dielectric.

14. The sensor for biomolecules of claim 4, wherein the antibodies are in direct contact with the electrolyte.

* * * * *